US008889155B2

(12) United States Patent
Okumura et al.

(10) Patent No.: US 8,889,155 B2
(45) Date of Patent: Nov. 18, 2014

(54) GEL COMPOSITION FOR TREATING MYCOSIS

(75) Inventors: Tomohiro Okumura, Fujieda (JP); Akiko Ochiai, Fujieda (JP); Keizo Sakuda, Bunkyo-ku (JP); Yoshiyuki Tatsumi, Kyoto (JP)

(73) Assignee: Kaken Pharmaceutical Co., Ltd., Tokyo (JP)

( * ) Notice: Subject to any disclaimer, the term of this patent is extended or adjusted under 35 U.S.C. 154(b) by 372 days.

(21) Appl. No.: 12/521,483

(22) PCT Filed: Dec. 28, 2007

(86) PCT No.: PCT/JP2007/075303
§ 371 (c)(1),
(2), (4) Date: Jun. 26, 2009

(87) PCT Pub. No.: WO2008/081940
PCT Pub. Date: Jul. 10, 2008

(65) Prior Publication Data
US 2010/0317695 A1  Dec. 16, 2010

(30) Foreign Application Priority Data
Dec. 28, 2006 (JP) .................... 2006-354626

(51) Int. Cl.
| *A61K 9/00* | (2006.01) |
| *A61K 47/32* | (2006.01) |
| *A61K 47/26* | (2006.01) |
| *A61K 47/10* | (2006.01) |
| *A61K 47/14* | (2006.01) |
| *A61K 31/454* | (2006.01) |
| *A61K 9/06* | (2006.01) |

(52) U.S. Cl.
CPC .............. *A61K 31/454* (2013.01); *A61K 47/32* (2013.01); *A61K 47/26* (2013.01); *A61K 47/10* (2013.01); *A61K 47/14* (2013.01); *A61K 9/06* (2013.01); *A61K 9/0014* (2013.01)
USPC ........................................................ 424/400

(58) Field of Classification Search
USPC ........................................................ 424/400
See application file for complete search history.

(56) References Cited

U.S. PATENT DOCUMENTS

| 5,601,839 A | 2/1997 | Quan et al. |
| 5,696,105 A * | 12/1997 | Hackler ................. 514/172 |
| 5,993,787 A * | 11/1999 | Sun et al. ................ 424/59 |
| 6,585,963 B1 * | 7/2003 | Quan et al. ............... 424/61 |
| 2007/0082375 A1 | 4/2007 | Tatsumi et al. |

FOREIGN PATENT DOCUMENTS

| EP | 0698606 A1 | 2/1996 |
| EP | 1205559 A1 | 5/2002 |
| JP | 60-61518 A | 9/1983 |
| JP | 60-061518 A | 4/1985 |
| JP | 63-290817 A | 11/1988 |
| JP | 02-264723 A | 4/1989 |
| JP | 02-264723 A | 10/1990 |
| JP | 5-148141 A | 11/1991 |
| JP | 05-148141 A | 6/1993 |
| JP | 10-59847 A | 3/1998 |
| JP | 10-507199 A | 7/1998 |
| WO | 94/26734 A1 | 11/1994 |
| WO | 01/07643 A1 | 2/2001 |

OTHER PUBLICATIONS

Y. Tatsumi, et al., "Therapeutic Efficacy of Topically Applied KP-103 against Experimental Tinea Unguium in Guinea Pigs in Comparison with Amorolfine and Terbinafine", Antimicrobial Agents and Chemotherapy, vol. 46, No. 12, pp. 3797-3801, Dec. 2001.
European Search Report dated Nov. 23, 2009, issued in European Application No. 07860506.0.
Office Action issued Feb. 4, 2013, in corresponding Japanese Patent Application No. 2008-552190.

* cited by examiner

*Primary Examiner* — Peter J Reddig
*Assistant Examiner* — Devang Thakor
(74) *Attorney, Agent, or Firm* — Sughrue Mion, PLLC

(57) ABSTRACT

The present invention provides a stable gel composition for mycosis treatment, with increased absorption and permeation of (2R,3R)-2-(2,4-difluorophenyl)-3-(4-methylenepiperidin-1-yl)-1-(1H-1,2,4-triazol-1-yl)-butan-2-ol into a target site (skin and nail). The gel composition for mycosis treatment, comprises (2R,3R)-2-(2,4-difluorophenyl)-3-(4-methylenepiperidin-1-yl)-1-(1H-1,2,4-triazol-1-yl)-butan-2-ol or an acid addition salt thereof, a lower alcohol, a polyhydric alcohol and a gel-forming polymer. The gel composition of the present invention increases permeation of the above compound into a target site and into the nail. The gel composition of the present invention allows the drug to be directly and rapidly absorbed and permeated into a target site in a constant manner, for mycosis treatment, particularly onychomycosis treatment.

17 Claims, 4 Drawing Sheets

GEL COMPOSITION FOR TREATING MYCOSIS

TECHNICAL FIELD

The present invention relates to a gel composition for mycosis treatment, which ensures good absorption and permeation of (2R,3R)-2-(2,4-difluorophenyl)-3-(4-methylenepiperidin-1-yl)-1-(1H-1,2,4-triazol-1-yl)-butan-2-ol (hereinafter also abbreviated as "KP-103") into the skin and nail. The present invention also relates to a gel composition for mycosis treatment, which is excellent in storage stability of this drug.

BACKGROUND ART

In the case of external preparations for treatment of superficial mycoses, their therapeutic effect is greatly influenced by each drug's ability to permeate the skin and nail. Particularly in the treatment of onychomycoses, oral antifungal preparations are mainly used because existing antifungal preparations for external use cannot achieve sufficient drug permeation into the thick keratin layer in the nail plate and hence cannot produce any antifungal effect on fungi in the nail. However, treatment via the oral route requires 3 to 6 months in terms of nail turnover. For this reason, there appear side effects such as digestive symptoms and/or hepatic dysfunction, and it is recommended to receive periodic examinations of liver function and blood during the treatment. This significantly reduces the compliance of patients.

On the other hand, the applicant has designed an antifungal compound, (2R,3R)-2-(2,4-difluorophenyl)-3-(4-methylenepiperidin-1-yl)-1-(1H-1,2,4-triazol-1-yl)-butan-2-ol (Patent Document 1). The applicant has also elucidated that KP-103 solutions (in 74% polyethylene glycol/25% ethanol) exert a therapeutic effect on onychomycoses (tinea unguium in guinea pigs), which was not achieved by conventional antifungal preparations for external use (Patent Document 2). In light of onychomycosis treatment, there has been a demand for the development of KP-103 preparations showing a higher curing effect than KP-103 solutions, wherein the preparations allow increased area and/or speed of absorption/permeation into the nails of fingers and toes, particularly into deformed nails, and thereby produce a curing effect within a short period of time. However, such external preparations for superficial mycoses with enhanced permeation have been difficult to develop. Particularly in the case of external preparations for onychomycoses, the same permeation effect as observed in the skin cannot apply to the nail because of differences in chemical structure between nail and skin. Thus, it has been difficult to improve drug permeation in the nail.

Patent Document 1: Japanese Patent No. 2768830
Patent Document 2: International Patent Publication No. WO01/07643

DISCLOSURE OF THE INVENTION

Problems to be Solved by the Invention

An object of the present invention is to provide an external therapeutic preparation for mycoses, which is excellent in absorption and permeation of KP-103 at a target site (skin and nail). Another object of the present invention is to provide a preparation, which ensures good storage stability of KP-103.

Means for Solving the Problems

As a result of extensive and intensive efforts made to develop preparations showing higher drug permeation than KP-103 solutions, the inventors of the present invention have found that KP-103 ensures remarkably increased drug permeation at a target site when formulated into a gel composition. This finding led to the completion of the present invention.

Thus, when compared to conventional solutions, the KP-103 gel composition of the present invention is excellent in drug permeation at a target site, particularly also excellent in permeation into the nail, and produces a therapeutic effect even on mycoses caused by fungi in the nail within a short period of time.

Namely, the present invention provides a gel composition for mycosis treatment, which comprises (2R,3R)-2-(2,4-difluorophenyl)-3-(4-methylenepiperidin-1-yl)-1-(1H-1,2,4-triazol-1-yl)-butan-2-ol or an acid addition salt thereof as an active ingredient, as well as a lower alcohol, a polyhydric alcohol and a gel-forming polymer.

BEST MODE FOR CARRYING OUT THE INVENTION

Figure 1:
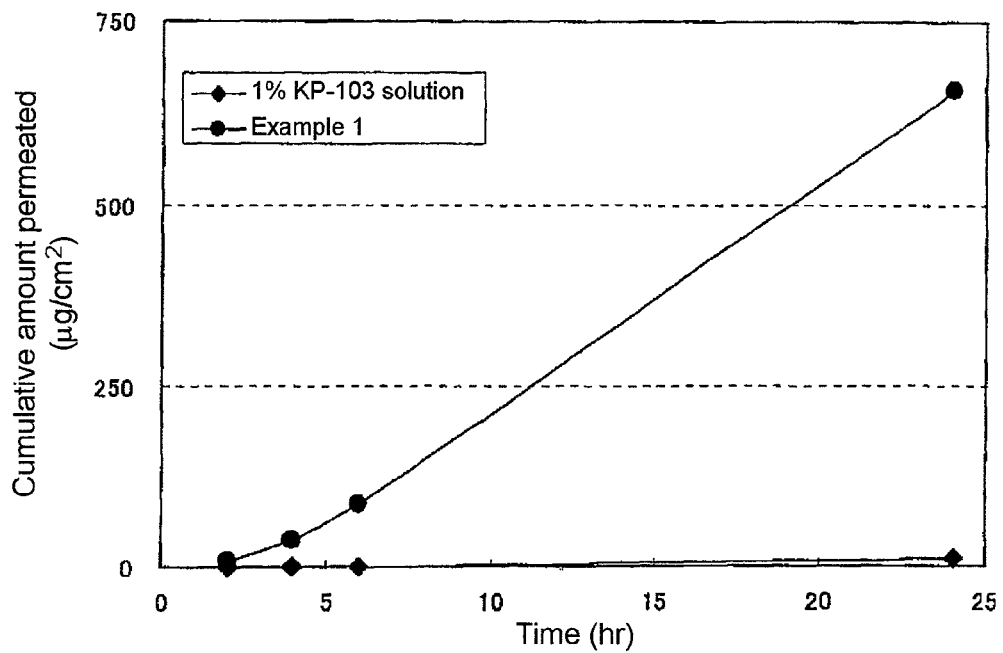
FIG. 1 shows the results of permeation test in nude mouse skin.

Preferred embodiments of the present invention are as follows.

According to one embodiment, the present invention provides such a gel composition as mentioned above, wherein the mycosis is onychomycosis.

According to another embodiment, the present invention provides such a gel composition as mentioned above, which further comprises a permeation enhancer.

According to yet another embodiment, the present invention provides such a gel composition as mentioned above, wherein the lower alcohol is one or more members selected from ethanol, isopropanol and butanol.

According to yet another embodiment, the present invention provides such a gel composition as mentioned above, wherein the polyhydric alcohol is one or more members selected from glycerine, 1,3-butylene glycol, propylene glycol, dipropylene glycol and triethylene glycol.

According to yet another embodiment, the present invention provides such a gel composition as mentioned above, wherein the content of the polyhydric alcohol is 20.0% to 90.0% by mass of the composition.

According to yet another embodiment, the present invention provides such a gel composition as mentioned above, wherein the permeation enhancer is one or more members selected from triacetin, sorbitan monooleate and polyoxyethylene sorbitan monooleate.

According to yet another embodiment, the present invention provides such a gel composition as mentioned above, wherein the content of the permeation enhancer is 1.0% to 30.0% by mass of the composition.

According to yet another embodiment, the present invention provides such a gel composition as mentioned above, wherein the gel-forming polymer is a member of carboxyvinyl polymer.

According to yet another embodiment, the present invention provides such a gel composition as mentioned above, which further comprises a neutralizing agent.

According to yet another embodiment, the present invention provides such a gel composition as mentioned above, wherein the content of the gel-forming polymer is 0.01% to 10.0% by mass of the composition.

According to yet another embodiment, the present invention provides such a gel composition as mentioned above, wherein the gel composition has a pH of about 6 to about 8.

According to yet another embodiment, the present invention provides such a gel composition as mentioned above, wherein the gel composition comprises 0.01% to 10.0% by mass of (2R,3R)-2-(2,4-difluorophenyl)-3-(4-methylenepiperidin-1-yl)-1-(1H-1,2,4-triazol-1-yl)-butan-2-ol or an acid addition salt thereof, 0.1% to 5.0% by mass of carboxyvinyl polymer, 10.0% to 30.0% by mass of a permeation enhancer, 15.0% to 50.0% by mass of a lower alcohol and 30.0% to 70.0% by mass of a polyhydric alcohol, in which the ingredients are given in % by mass of the composition, and wherein the gel composition has a pH of about 6 to about 8.

KP-103 or an acid addition salt thereof, which is an active ingredient in the gel composition of the present invention, may be prepared in a known manner, for example, as described in Japanese Patent No. 2768830.

Examples of an acid which can form an acid addition salt of KP-103 include inorganic acids such as hydrochloric acid, sulfuric acid, hydrobromic acid, phosphoric acid and nitric acid, as well as organic acids such as formic acid, acetic acid, propionic acid, succinic acid, glycolic acid, lactic acid, malic acid, tartaric acid, citric acid, maleic acid, phthalic acid, phenylacetic acid, benzoic acid, salicylic acid, methanesulfonic acid, toluenesulfonic acid, benzenesulfonic acid, oxalic acid and trifluoroacetic acid. Among them, an acid which can form a pharmaceutically acceptable acid addition salt may be selected as appropriate.

In the preparation of the present invention, two or more of KP-103 and acid addition salts thereof may be used in combination.

As used herein, the term "gel composition" is intended to mean a flexible semi-solid preparation in which a gel-forming polymer aggregates to hold plenty of solvent therein. An embodiment in which the preparation is converted into such a gel composition after being applied to the affected nail and/or skin surface also falls within the gel composition of the present invention.

As used herein, the ratio of individual ingredients is intended to mean the ratio at the preparation stage in a case where the ingredients are formulated in the form of a gel composition, or alternatively, the ratio at the application stage in a case where the ingredients are converted into a gel composition after being applied. In the latter case where the ingredients are converted into a gel composition after being applied, the ratio at the preparation stage may be determined in previous consideration of the amount of volatilized solvent, etc.

As used herein, the term "gel-forming polymer" is intended to mean a polymer such as a member of carboxyvinyl polymer, carboxymethylcellulose, carboxymethylcellulose sodium, polyvinyl alcohol, polyvinylpyrrolidone, hydroxypropylcellulose, hydroxypropylmethylcellulose, methylvinyl ether-maleic anhydride copolymer, sodium alginate, propylene glycol alginate, pectin, xanthan gum, locust bean gum, guar gum, arabinogalactan, sodium hyaluronate, or polyethylene oxide. Among them, preferred is a member of carboxyvinyl polymer, and more preferred is carboxyvinyl polymer.

As used herein, the phrase "member of carboxyvinyl polymer" is intended to mean a polymer having the following acrylic acid monomer unit appearing in carboxyvinyl polymer:

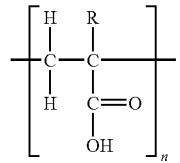

[Formula 1]

(wherein R represents hydrogen or methyl)
and includes carboxyvinyl polymer, as well as methacrylic acid polymers, methacrylic acid-acrylic acid copolymers, esters thereof (in which carboxyl groups are partially esterified with an alkyl group containing 10 to 30 carbon atoms), and (metha)acrylic acid-maleic acid copolymers. As used here, the term "(metha)acrylic acid" is intended to mean both "acrylic acid" and "methacrylic acid."

Members of carboxyvinyl polymer may be commercially available products. In the case of carboxyvinyl polymer, examples include AQUPEC®, Carbopol®, Junlon®, Hiviswako® and Synthalen®.

The content of the above gel-forming polymer in the gel composition of the present invention is preferably 0.01% to 10.0% by mass, and more preferably 0.1% to 5.0% by mass.

When carboxyvinyl polymer or the like is used as a gel-forming polymer, it is necessary in some cases to adjust the pH of the composition by addition of a neutralizing agent for the purpose of gel formation. Examples of a neutralizing agent for this purpose include diisopropanolamine, monoethanolamine, diethanolamine, triethanolamine and sodium hydroxide. The neutralizing agent is preferably selected depending on the type of polymer. For example, a neutralizing agent preferred for carboxyvinyl polymer is diisopropanolamine. Moreover, the gel composition of the present invention generally has a pH of about 2 to about 11, preferably about 4 to about 11, more preferably about 5 to about 9, and even more preferably about 6 to about 8. As used here, the term "pH" is intended to mean the directly measured pH of the composition, or alternatively, the pH of a 50-fold dilution in water (or the supernatant pH measured after centrifugation to remove insoluble materials, if any) when the pH cannot be directly measured.

The content of the active ingredient(s) in the gel composition of the present invention is preferably 0.001% to 20.0% by mass, and more preferably 0.01% to 10.0% by mass.

In the present invention, the "lower alcohol" is not limited in any way and may be selected as appropriate for the intended purpose, as long as it is in liquid form at normal temperature.

More specifically, such a lower alcohol may be a commonly-used $C_1$-$C_4$ alcohol, and examples include methanol, ethanol (including denatured alcohol), propanol, butanol, isopropanol and isobutanol. Among them, preferred are ethanol, isopropanol, butanol and the like, and particularly preferred is ethanol. These lower alcohols may be used either alone or in combination. In terms of drug storage stability, preferred are anhydrous alcohols, e.g., anhydrous ethanol.

The content of the above lower alcohol(s) in the gel composition of the present invention may be the amount required to dissolve KP-103, and it is preferably 10.0% to 70.0% by mass, more preferably 15.0% to 50.0% by mass, and even more preferably 18.0% to 25.0% by mass.

In the present invention, the "polyhydric alcohol" is not limited in any way and may be selected as appropriate for the intended purpose, as long as it is in liquid form at normal temperature.

Specific examples of such a polyhydric alcohol include glycerine, 1,3-butylene glycol, propylene glycol, dipropylene glycol, triethylene glycol, isopropylene glycol, ethylene glycol, diethylene glycol, diethylene glycol monoalkyl ether, polyethylene glycol, polypropylene glycol, polyethylene glycol-polypropylene glycol, propylene glycol dicaprylate, polyoxyethylene hydrogenated castor oil, diglycerine, triglycerine, and polyglycerine. Among them, preferred are non-volatile polyhydric alcohols such as glycerine, 1,3-butylene glycol, propylene glycol, dipropylene glycol, triethylene glycol, isopropylene glycol, ethylene glycol, diethylene glycol, diethylene glycol monoalkyl ether, polyethylene glycol, polypropylene glycol, polyethylene glycol-polypropylene glycol, diglycerine, triglycerine and polyglycerine, and particularly preferred are glycerine, 1,3-butylene glycol, propylene glycol, dipropylene glycol and triethylene glycol. These polyhydric alcohols may be used either alone or in combination. In terms of drug storage stability, preferred are anhydrous polyhydric alcohols, e.g., concentrated glycerin.

The content of the above polyhydric alcohol(s) in the gel composition of the present invention is preferably 20.0% to 90.0% by mass, and more preferably 30.0% to 70.0% by mass.

The preferred amount of polyhydric alcohol(s) will vary depending on their type and relationship with other ingredients. In a case where carboxyvinyl polymer is used as a gel-forming polymer, it is desirable to use large amounts of one or more polyhydric alcohols such as glycerine, 1,3-butylene glycol, propylene glycol, dipropylene glycol and triethylene glycol if the content of carboxyvinyl polymer is low.

In the present invention, the "permeation enhancer" may be selected as appropriate for the intended purpose.

Specific examples of such a permeation enhancer include triacetin, glycerine, sorbitan esters of fatty acid, sorbitan monostearate, polyoxyethylene sorbitan monostearate, sorbitan monooleate, glyceryl monostearate, polyoxyethylene sorbitan monooleate, polyoxyethylene cetyl ether, polyethylene glycol monostearate, urea, sodium lauryl sulfate, sodium sulfide, sodium thioglycolate (2%), sodium thiosulfate and sodium benzoate, as well as monoterpenes, alcohols, polyhydric alcohols, alkylpyrrolidones, surfactants, hydrocarbons, esters, triglycerides, fatty acids, and fatty acid esters. Among them, preferred are permeation enhancers such as triacetin, sorbitan monooleate and polyoxyethylene sorbitan monooleate, and particularly preferred is triacetin. These permeation enhancers may be used either alone or in combination.

The content of the above permeation enhancer(s) in the composition of the present invention is preferably 1.0% to 30.0% by mass, and more preferably 10.0% to 30.0% by mass.

The gel composition of the present invention may be either aqueous or non-aqueous. In terms of the storage stability of KP-103, the water content in the gel composition is preferably 50% by mass or less, more preferably 20% by mass or less, and even more preferably 5% by mass or less, provided that water which is associated or enters during operation is permitted in actual cases. As used here, the term "storage stability" is intended to mean that KP-103 remains stable even when temperature rise or the like is caused by environmental or temperature changes during storage period.

The gel composition of the present invention may be prepared to further comprise various known additives, i.e., antioxidants, preservatives, flavorings, coloring agents and so on, as long as these additives do not impair the effect of the gel composition of the present invention. Examples of such additives include, but are not limited to, antioxidants such as tocopherol, butylhydroxyanisole, dibutylhydroxytoluene or benzotriazole, and preservatives such as paraoxybenzoic acid ester, sodium edetate, dl-camphor, chlorobutanol, thimerosal, thymol, phenol, phenylethyl alcohol or l-menthol.

The gel composition of the present invention can be prepared by standard procedures for preparation of a gel composition. For example, a gel-forming polymer, a polyhydric alcohol and a lower alcohol may optionally be stirred under warming or heating to disperse the polymer, followed by addition of a neutralizing agent, if necessary, to form a gel. Independently of this, KP-103 may be dissolved in a lower alcohol and, if necessary, supplemented with a permeation enhancer. The resulting KP-103 mixture may be added to the above gel, followed by kneading to obtain the gel composition of the present invention. The neutralizing agent may be added after the KP-103 mixture is combined with the gel. Alternatively, KP-103, a lower alcohol, a polyhydric alcohol and a gel-forming polymer may be mixed and, if necessary, supplemented with a permeation enhancer. The mixture may optionally be stirred under warming or heating to disperse the polymer, followed by addition of a neutralizing agent, if necessary, to obtain the gel composition of the present invention.

The gel composition of the present invention may be applied to a target site (e.g., nail for onychomycosis treatment) and optionally further covered to treat mycoses.

The gel composition of the present invention may be applied to a target site, either directly or by spraying. In another embodiment of application, the gel composition may be expanded into a sheet form or coated over a support and then applied to a target site.

In yet another embodiment, the solvent may be dried to give a gel composition after application to a target site.

As used herein, the term "mycosis" refers to a fungal infection caused by a strain of *Candida* sp., *Trichophyton* sp., *Microsporum* sp., *Epidermophyton* sp., *Malassezia* sp., *Cryptococcus neoformans*, *Aspergillus* sp. or *Blastomyces* sp.

As used herein, the term "onychomycosis" refers to a syndrome that develops as a result of fungal invasion and growth in human or animal nails. The major fungi responsible for human onychomycosis are *Trichophyton rubrum* and *Trichophyton mentagrophytes* belonging to *Trichophyton* sp. In some rare cases, fungi of *Microsporum* sp., *Epidermophyton* sp., *Candida* sp., *Aspergillus* sp., *Fusarium* sp., *Cladosporium* sp. or *Penicillium* sp. are responsible for human onychomycosis.

The preparation of the present invention is indicated for the treatment of tinea unguium caused by fungi of *Trichophyton* sp., nail candidiasis caused by fungi of *Candida* sp., as well as onychomycoses caused by other fungi.

As used herein, the term "nail" covers nail plate, nail bed and nail matrix, and is intended to also mean their surrounding tissues, i.e., lateral nail fold and posterior nail fold, as well as their surrounding skin areas, i.e., eponychium and hyponychium.

Although the dose of the gel composition of the present invention may be adjusted, as appropriate, depending on the size of the affected area and the type of symptom, the gel composition of the present invention exerts a therapeutic effect on mycoses in the skin and nail at a lower dose and within a shorter period than in conventional preparations, because the gel composition of the present invention is very excellent in its permeation ability and also shows very high permeation into the nail.

Detailed explanation is given below on preferred examples of the present invention. It should be noted that the following examples are provided for illustrative purposes only and are not intended to limit the scope of the claimed invention.

EXAMPLES 1 to 5

In Examples 1 to 5 shown below, individual ingredients were mixed to prepare a gel composition according to the following formula. First, among the ingredients, KP-103 was dissolved in ethanol. To this solution, triacetin, glycerine (and 1,3-butylene glycol) were added and mixed, followed by addition of carboxyvinyl polymer. The mixture was warmed to disperse the carboxyvinyl polymer. After cooling, diisopropanolamine was added to prepare a gel composition. The carboxyvinyl polymer used was Hiviswako® 104, which is a product of Wako Pure Chemical Industries, Ltd., Japan. To measure the pH of each gel composition, 0.1 g of the gel composition was diluted in 5 mL water and measured with a pH meter (F-23, Horiba, Ltd., Japan).

Based on the mass of the whole composition to be prepared, which was set to 100 g, individual ingredients were mixed at the ratio indicated below to prepare the composition (gel preparation) of Example 1 according to the present invention.

TABLE 1

| | |
|---|---|
| KP-103 | 1.0 g |
| Triacetin | 10.0 g |
| Concentrated glycerin | 63.475 g |
| Carboxyvinyl polymer | 0.375 g |
| Diisopropanolamine | 0.15 g |
| Anhydrous ethanol | q.s. |

The above composition was found to have a pH of 7.4.

"q.s." is intended to mean the amount required for the whole composition to have a mass of 100 g. The same also applies hereinafter.

Individual ingredients were mixed at the ratio indicated below to prepare the composition (gel preparation) of Example 2.

TABLE 2

| | |
|---|---|
| KP-103 | 0.1 g |
| Triacetin | 10.0 g |
| Concentrated glycerin | 63.475 g |
| Carboxyvinyl polymer | 0.375 g |
| Diisopropanolamine | 0.15 g |
| Anhydrous ethanol | q.s. |

The above composition was found to have a pH of 6.8.

Individual ingredients were mixed at the ratio indicated below to prepare the composition (gel preparation) of Example 3.

TABLE 3

| | |
|---|---|
| KP-103 | 1.0 g |
| Triacetin | 15.0 g |
| Concentrated glycerin | 35.0 g |
| 1,3-Butylene glycol | 25.0 g |
| Carboxyvinyl polymer | 1.0 g |
| Diisopropanolamine | 0.2 g |
| Anhydrous ethanol | q.s. |

The above composition was found to have a pH of 6.7.

Individual ingredients were mixed at the ratio indicated below to prepare the composition (gel preparation) of Example 4.

TABLE 4

| | |
|---|---|
| KP-103 | 1.0 g |
| Triacetin | 15.0 g |
| Concentrated glycerin | 35.0 g |
| 1,3-Butylene glycol | 25.0 g |
| Carboxyvinyl polymer | 1.0 g |
| Diisopropanolamine | 0.2 g |
| Tocopherol | 0.01 g |
| Anhydrous ethanol | q.s. |

The above composition was found to have a pH of 6.7.

Individual ingredients were mixed at the ratio indicated below to prepare the composition (gel preparation) of Example 5.

TABLE 5

| | |
|---|---|
| KP-103 | 1.0 g |
| Triacetin | 15.0 g |
| Concentrated glycerin | 35.0 g |
| Carboxyvinyl polymer | 1.0 g |
| Diisopropanolamine | 0.4 g |
| Anhydrous ethanol | q.s. |

The above composition was found to have a pH of 7.1.

EXAMPLES 6 to 11

Compositions (gel preparations) were prepared based on the formula used in Example 4 by varying the amount of KP-103 and the type of carboxyvinyl polymer as indicated in the table below. Carbopol® 940 is a product of Noveon, Inc. and Synthalen® K is a product of 3V SIGMA.

TABLE 6

| | Example 6 | Example 7 | Example 8 | Example 9 | Example 10 | Example 11 |
|---|---|---|---|---|---|---|
| KP-103 | 1 g | 3 g | 3 g | 5 g | 5 g | 5 g |
| Carboxyvinyl polymer (trade name) | 1 g (Carbopol 940) | 1 g (Hiviswako 104) | 1 g (Carbopol 940) | 1 g (Hiviswako 104) | 1 g (Carbopol 940) | 1 g (Synthalen K) |
| Triacetin | 15 g | 15 g | 15 g | 15 g | 15 g | 15 g |
| Anhydrous ethanol | q.s. | q.s. | q.s. | q.s. | q.s. | q.s. |
| Concentrated glycerin | 35 g | 35 g | 35 g | 35 g | 35 g | 35 g |
| 1,3-Butylene glycol | 25 g | 25 g | 25 g | 25 g | 25 g | 25 g |
| Diisopropanolamine | 0.2 g | 0.2 g | 0.2 g | 0.2 g | 0.2 g | 0.2 g |
| Tocopherol | 0.01 g | 0.03 g | 0.03 g | 0.05 g | 0.05 g | 0.05 g |

EXAMPLES 12 to 15

Compositions (gel preparations) were prepared based on the formula used in Example 4 by varying the amounts of polyhydric alcohols, except for concentrated glycerin, as indicated in the table below.

TABLE 7

|  | Example 12 | Example 13 | Example 14 | Example 15 |
|---|---|---|---|---|
| KP-103 | 1 g | 1 g | 1 g | 1 g |
| Carboxyvinyl polymer (trade name) | 1 g (Hiviswako 104) | 1 g (Hiviswako 104) | 1 g (Hiviswako 104) | 1 g (Hiviswako 104) |
| Triacetin | 15 g | 15 g | 15 g | 15 g |
| Anhydrous ethanol | q.s. | q.s. | q.s. | q.s. |
| Concentrated glycerin | 35 g | 35 g | 35 g | 35 g |
| 1,3-Butylene glycol | 5 g | — | 15 g | — |
| Dipropylene glycol | 20 g | 20 g | — | 15 g |
| Triethylene glycol | — | 5 g | 10 g | 10 g |
| Tocopherol | 0.2 g | 0.2 g | 0.2 g | 0.2 g |

EXAMPLES 16 to 19

Compositions (gel preparations) were prepared based on the formulae used in Examples 1 and 5 by varying the amounts of carboxyvinyl polymer and other ingredients as indicated in the table below.

TABLE 8

|  | Example 16 | Example 17 | Example 18 | Example 19 | Example 20 | Example 21 |
|---|---|---|---|---|---|---|
| KP-103 | 1 g | 1 g | 1 g | 1 g | 1 g | 1 g |
| Carboxyvinyl polymer (trade name) | 0.25 g (Hiviswako 104) | 0.5 g (Hiviswako 104) | 0.75 g (Hiviswako 104) | 2 g (Hiviswako 104) | 0.01 g (Hiviswako 104) | 0.1 g (Hiviswako 104) |
| Triacetin | 10 g | 10 g | 15 g | 15 g | 15 g | 15 g |
| Anhydrous ethanol | 25 g | 25 g | q.s. | q.s. | q.s. | q.s. |
| Concentrated glycerin | q.s. | q.s. | 35 g | 35 g | 35 g | 35 g |
| Diisopropanolamine | 0.05 g | 0.1 g | 0.2 g | 0.8 g | 0.002 g | 0.02 g |

Note: Examples 20 and 21 correspond to embodiments where the resulting preparation is converted into a gel composition after being applied. In these examples, volatile ingredients (e.g., lower alcohol) were volatilized after application to give a gel composition.

The gel compositions from Examples 6 to 21 were measured for their pH in the same manner as used in other examples. The results obtained are shown in Tables 9 and 10.

TABLE 9

| | Example 6 | Example 7 | Example 8 | Example 9 | Example 10 | Example 11 | Example 12 | Example 13 |
|---|---|---|---|---|---|---|---|---|
| pH | 6.6 | 7.0 | 6.6 | 6.9 | 6.6 | 6.3 | 6.6 | 6.2 |

TABLE 10

| | Example 14 | Example 15 | Example 16 | Example 17 | Example 18 | Example 19 | Example 20 | Example 21 |
|---|---|---|---|---|---|---|---|---|
| pH | 6.6 | 6.7 | 7.0 | 7.1 | 7.0 | 6.5 | 7.1 | 7.0 |

EXPERIMENTAL EXAMPLE 1

Permeation test in animal model (nude mouse skin) 1

The compositions (gel preparations) according to the present invention were tested for their permeation into nude mouse skin in the following manner.

Nude mouse skin was sandwiched between side-by-side diffusion cells (contact area: about 0.95 cm$^2$). The diffusion cell on the donor side was filled with the gel preparation (Example 1), while the diffusion cell on the receiver side was filled with physiological saline. The temperature of circulating water on the receiver side was set at 37° C. to warm the physiological saline on the receiver side. The physiological saline on the receiver side was sampled over time and measured for the amount of drug permeation using a high-performance liquid chromatography system. As a control, a 1% KP-103 solution (in 74% polyethylene glycol/25% ethanol) was tested in the same manner. The test results obtained are shown in FIG. 1.

As shown in FIG. 1, when compared to the 1% KP-103 solution, the composition (gel preparation) of the present invention was found to allow about a 65-fold greater amount of KP-103 to permeate through the skin over 24 hours after initiation of the test.

EXPERIMENTAL EXAMPLE 2

Permeation Test in Animal Model (Nude Mouse Skin) 2

The same test as shown in Experimental Example 1 was repeated, except that the temperature of circulating water on the receiver side was set at 32° C. and the compositions (gel preparations) of the present invention indicated in the table below were used.

As shown in the table below, when compared to the 1% KP-103 solution, the compositions (gel preparations) of the present invention were found to allow about a 23- to 65-fold greater amount of KP-103 to permeate through the skin over 24 hours after initiation of the test.

TABLE 11

|  | Comparative Example: solution | Example 3 | Example 4 | Example 5 | Example 6 | Example 7 |
|---|---|---|---|---|---|---|
| Cumulative amount permeated µg/cm$^2$ | 1.6 | 48 | 50 | 50 | 52 | 64 |
| Steady state flux µg/cm$^2$/h | 0.08 ± 0.08 | 1.92 ± 1.20 | 2.31 ± 0.90 | 1.66 ± 1.06 | 2.57 ± 0.90 | 3.35 ± 1.04 |

|  | Example 9 | Example 12 | Example 13 | Example 14 | Example 15 |
|---|---|---|---|---|---|
| Cumulative amount permeated µg/cm$^2$ | 104 | 36 | 46 | 49 | 40 |
| Steady state flux µg/cm$^2$/h | 6.44 ± 2.04 | 1.39 ± 0.73 | 1.62 ± 0.98 | 1.89 ± 0.77 | 1.63 ± 0.76 |

EXPERIMENTAL EXAMPLE 3

Permeation Test in Animal Model (Pig Nail) 1

The compositions (gel preparations) according to the present invention were tested for their permeation into pig nail in the following manner.

Dry pig nail was immersed in physiological saline at 37° C. and the lateral part of the nail was then removed off with a pair of scissors. Using a micro-router, the nail was scraped from its back surface (on the finger side) to give a uniform thickness, thereby preparing a round pig nail disk (diameter: about 15 mm, thickness: 0.5-1 mm).

This nail disk was sandwiched between side-by-side diffusion cells (contact area: about 0.95 cm$^2$). The diffusion cell on the donor side was filled with the gel preparation (Example 1), while the diffusion cell on the receiver side was filled with physiological saline. The temperature of circulating water on the receiver side was set at 37° C. to warm the physiological saline on the receiver side. The physiological saline on the receiver side was sampled over time and measured for the amount of KP-103 permeation using a high performance liquid chromatography-mass spectrometer. As a control, a 1% KP-103 solution was tested in the same manner. The test results obtained are shown in FIG. 2.

Figure 2:
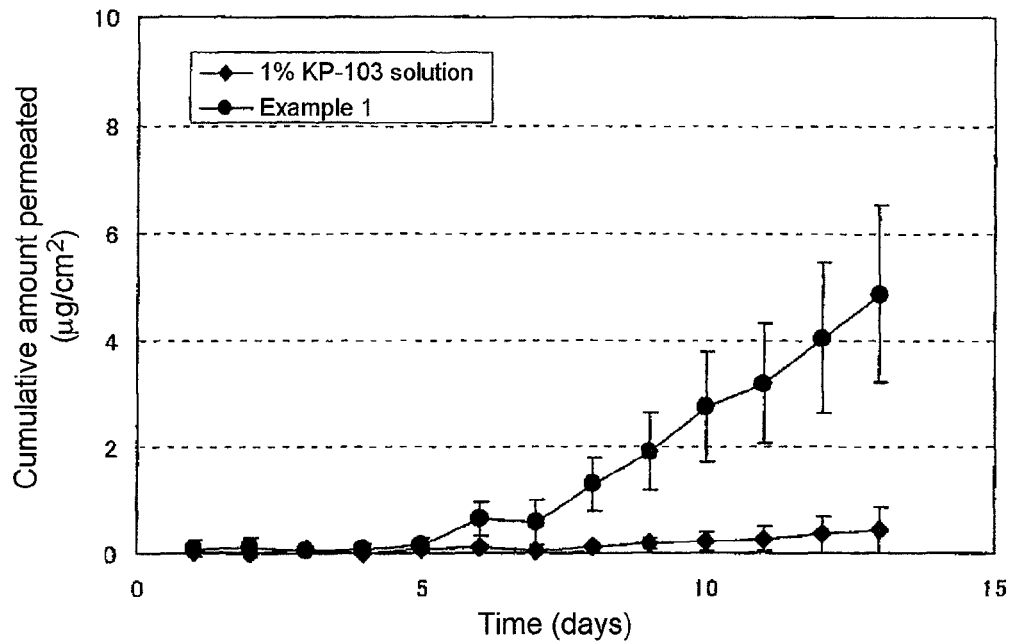
FIG. 2 shows the results of permeation test in pig nail.

As shown in FIG. 2, in the composition (gel preparation) of the present invention, the cumulative amount of KP-103 permeated through the nail was 4.9 µg/cm$^2$ over 13 days after initiation of the test, and the steady state flux was 0.77±0.27 µg/cm$^2$/day. On the other hand, in the 1% KP-103 solution, the cumulative amount of KP-103 permeated through the nail was 0.4 µg/cm2 and the steady state flux was 0.06±0.06 µg/cm$^2$/day.

Namely, when compared to the 1%. KP-103 solution, the composition (gel preparation) of the present invention was found to allow about a 12-fold greater amount of KP-103 to permeate through the nail.

EXPERIMENTAL EXAMPLE 4

Permeation Test in Animal Model (Pig Nail) 2

The same test as shown in Experimental Example 3 was repeated, except that the composition (gel preparation) of the present invention from Example 4 was used.

As a result, in the composition (gel preparation) of the present invention, the cumulative amount of KP-103 permeated through the nail was 8.5 µg/cm$^2$ over 13 days after initiation of the test, and the steady state flux was 0.98±0.26 µg/cm$^2$/day.

EXPERIMENTAL EXAMPLE 5

Permeation Test in Animal Model (Pig Nail) 3

The same test as shown in Experimental Example 3 was repeated, except that the compositions (gel preparations) of the present invention from Examples 7 and 9 were used and the cumulative amount permeated was measured over 12 days after initiation of the test.

As a result, in the compositions (gel preparations) of the present invention from Examples 7 and 9, the cumulative amount of KP-103 permeated through the nail was 5.7 µg/cm$^2$ and 3.1 µg/cm$^2$, respectively, over 12 days after initiation of the test, and the steady state flux was 0.66±0.27 µg/cm$^2$/day and 0.49±0.10 µg/cm$^2$/day, respectively.

EXPERIMENTAL EXAMPLE 6

Reducing Effect on Fungal Counts in the Nail of Animal Model (Dermatophyte-Infected Pig Nail)

The compositions (gel preparations) according to the present invention were evaluated for their reducing effect on fungal counts in the nail in the following manner.

Dry pig nail was immersed in hot water at 40° C. for 3 hours and the lateral part of the nail was then removed off with a pair of scissors. Using a micro-router, the nail was scraped from its back surface (on the finger side) to give a uniform thickness, thereby preparing a round pig nail disk (diameter: 22 mm, weight: 120-130 mg).

This nail disk was sandwiched with its scraped surface up between upper and lower cells of a vertical Franz diffusion cell (opening diameter: 15 mm). A paper disk immersed with 100 µL (10$^7$ microconidia) of *T. mentagrophytes* KD-04 solution was placed and the upper cell was sealed with a silicon plug. The nail disk was incubated at 30° C. for 3 days and infected with the dermatophytes.

Figure 3:
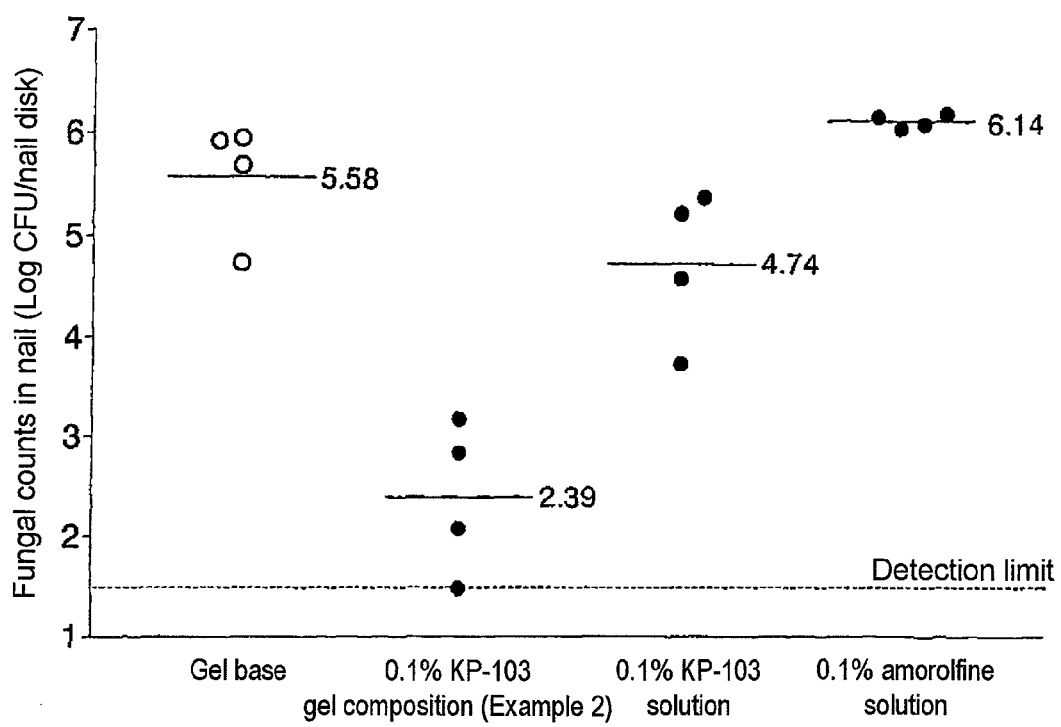
FIG. 3 shows the results of fungal count reduction in dermatophyte-infected pig nail.

The infected nail was removed from the Franz diffusion cell and sandwiched again with its dermatophyte-infected side down in the Franz diffusion cell. After the lower cell was injected with physiological saline (10 mL), the upper cell was charged with 300 µL of a gel base (the formula of Example 2, except for the drug), a 0.1% KP-103 gel preparation (Example 2), a 0.1% KP-103 solution (in 74.9% polyethylene glycol/25% ethanol) or a 0.1% amorolfine solution (in 74.9% polyethylene glycol/25% ethanol). The physiological saline in the lower cell was stirred with a magnetic stirrer at 200 rpm and tap water at 32° C. was circulated around the lower cell to incubate the nail at a constant temperature. At 14 days after addition of the preparation, the infected nail was collected and cut into pieces with a pair of scissors. The nail pieces were introduced into a glass homogenizer and homogenized in 3 mL phosphate-buffered physiological saline (TAKARA SHUZO Co., Ltd., Japan) containing 0.25% trypsin (derived from porcine pancreas, MP Biomedicals). After incubation at 37° C. for 1 hour, the resulting homogenate was used as the initial solution and diluted with phosphate-buffered physiological saline to prepare 10-fold serial dilutions. The initial solution or dilutions (100 µL) were each applied onto a GPLP agar plate (Wako Pure Chemical Industries, Ltd., Japan) containing 50 µg/mL chloramphenicol (Wako Pure Chemical Industries, Ltd., Japan) and 100 µg/mL gentamicin (Schering-Plough), followed by incubation at 30° C. for 7 days. After incubation, the number of colonies appearing (CFU, colony forming unit) was counted (detection limit: 30 colonies/paw) and multiplied by the dilution factor to calculate fungal counts in the nail. The fungal counts in the nail were analyzed for statistical significance between groups by one-way ANOVA, followed by Tukey's multiple comparison test. The results obtained are shown in FIG. 3 and summarized in Table 12. In FIG. 3, fungal counts in the nail were plotted for each treated group, with the average count being indicated with a line and a numerical value.

TABLE 12

| Analyte | N | Average count in the nail (Log CFU ± SD) |
|---|---|---|
| Gel base | 4 | 5.58 ± 0.49 |
| 0.1% KP-103 gel preparation (Example 2) | 4 | 2.39 ± 0.76** |
| 0.1% KP-103 solution | 4 | 4.74 ± 0.75 |
| 0.1% Amorolfine solution | 4 | 6.14 ± 0.06 |

**denotes statistical significance at a significance level of 0.01% versus the gel base, 0.1% KP-103 solution and 0.1% amorolfine solution.

As shown in FIG. 3 and Table 12, a significant reducing effect on fungal counts in the nail was observed in the infected pig nail upon treatment with the 0.1% KP-103 gel preparation for 14 days, when compared to the gel base. This effect was significantly higher than that of the 0.1% KP-103 solution and the 0.1% amorolfine solution. From the results of the permeation test in pig nail (FIG. 2), it was inferred that the excellent effect of the 0.1% KP-103 gel preparation to reduce fungal counts in the nail would be due to good permeation of KP-103 into the nail achieved by this preparation.

EXPERIMENTAL EXAMPLE 7

Reducing Effect on Fungal Counts in the Nail of Animal Model (Dermatophyte-Infected Guinea Pig Nail)

The compositions (gel preparations) according to the present invention were evaluated for their reducing effect on fungal counts in the nail in the following manner.

(1) Preparation of Fungal Inoculum and Creation of Guinea Pig Tinea Unguium Model Brain heart infusion agar medium (Nissui Pharmaceutical Co., Ltd., Japan) was overlaid with a Millipore filter (HA, 47 mm diameter, 0.45 µm, Millipore), onto which 2×10$^6$ microconidia of *Trichophyton mentagrophytes* strain SM-110 were then smeared, followed by incubation in the presence of 17% $CO_2$ at 30° C. for 7 days. After incubation, a proper amount of 0.05% Tween 80-containing physiological saline was added dropwise onto the filter and the fungal surface was scratched with a platinum loop to release arthrospores. A solution containing these arthrospores was transferred to a glass homogenizer and then homogenized. The number of arthrospores in the arthrospore suspension was counted with a hemacytometer and the suspension was adjusted to a density of 1×10$^8$ arthrospores/mL, which was used as an inoculum.

A guinea pig tinea unguium model was created according to the method of Tatsumi et al. (Antimicrobial Agents and Chemotherapy 46:3797-3801, 2002) with minor modifications. Namely, after light abrasions were made with a sandpaper in the interdigital and plantar skin of male Hartley guinea pigs (5 weeks of age), paper disks (Whatman AAdisk cut to 8×4 mm size) immersed with the above inoculum were inserted into the interdigital spaces and a paper disk (Whatman AAdisk, diameter: 13 mm) immersed with the above inoculum (100 µL) was covered over the plantar surface. These paper disks were then fixed with a Self-adhering-Foam Pad (Restone 1560M, 3M) and an adhesive elastic cloth bandage (Elastpore, Nichiban Co., Ltd., Japan). At 21 days after infection, the paper disks and bandage were removed. The guinea pigs were allowed to stand until 60 days after infection, whereby the dermatophytes were allowed to invade within the nail plate.

(2) Treatment of Guinea Pig Tinea Unguium by External Application (Dose-Dependence Study)

The test substances used were the KP-103 (1%, 3% and 5%) gel preparations shown in Examples 4, 7 and 9. Starting from 60 days after infection, each test substance (30 µL per paw) was externally applied to the nail once a day for successive 21 days.

(3) Evaluation of Efficacy on Tinea Unguium

The effect on tinea unguium was evaluated in the following manner.

At 7 days after the last treatment, the animals were sacrificed. The hind paws were taken from each animal and sufficiently cleaned with 70% ethanol-immersed cotton. Nails were excised and measured for their weight. The nails were cut into fine pieces with a pair of scissors and transferred to a glass homogenizer, followed by addition of phosphate-buffered physiological saline (Phosphate Buffered Salts, TAKARA BIO) containing 0.25% porcine pancreatic trypsin (MP Biomedicals) in a volume of 1 mL per 50 mg of nail weight. The nail pieces were homogenized and allowed to stand at 37° C. for 1 hour. This nail suspension was used as the initial solution and diluted with 0.05% Tween 80-containing physiological saline to prepare 10-fold serial dilutions. The initial solution or dilutions (100 µL) were each applied onto GPLP medium (Wako Pure Chemical Industries, Ltd., Japan) (25 mL) containing 50 µg/mL chloramphenicol (Wako Pure Chemical Industries, Ltd., Japan), 100 µg/mL gentamicin (Schering-Plough), 50 µg/mL 5-fluorocytosine (Wako Pure Chemical Industries, Ltd., Japan) and 1 mg/mL cycloheximide (Wako Pure Chemical Industries, Ltd., Japan), followed by incubation at 30° C. for 7 days. After incubation, the number of colonies (CFU) appearing on the medium was counted and multiplied by the dilution factor to calculate fungal counts in the nail. If the number of colonies appearing on the plate is 1 or less, such a case is considered as fungus-negative.

Figure 4:
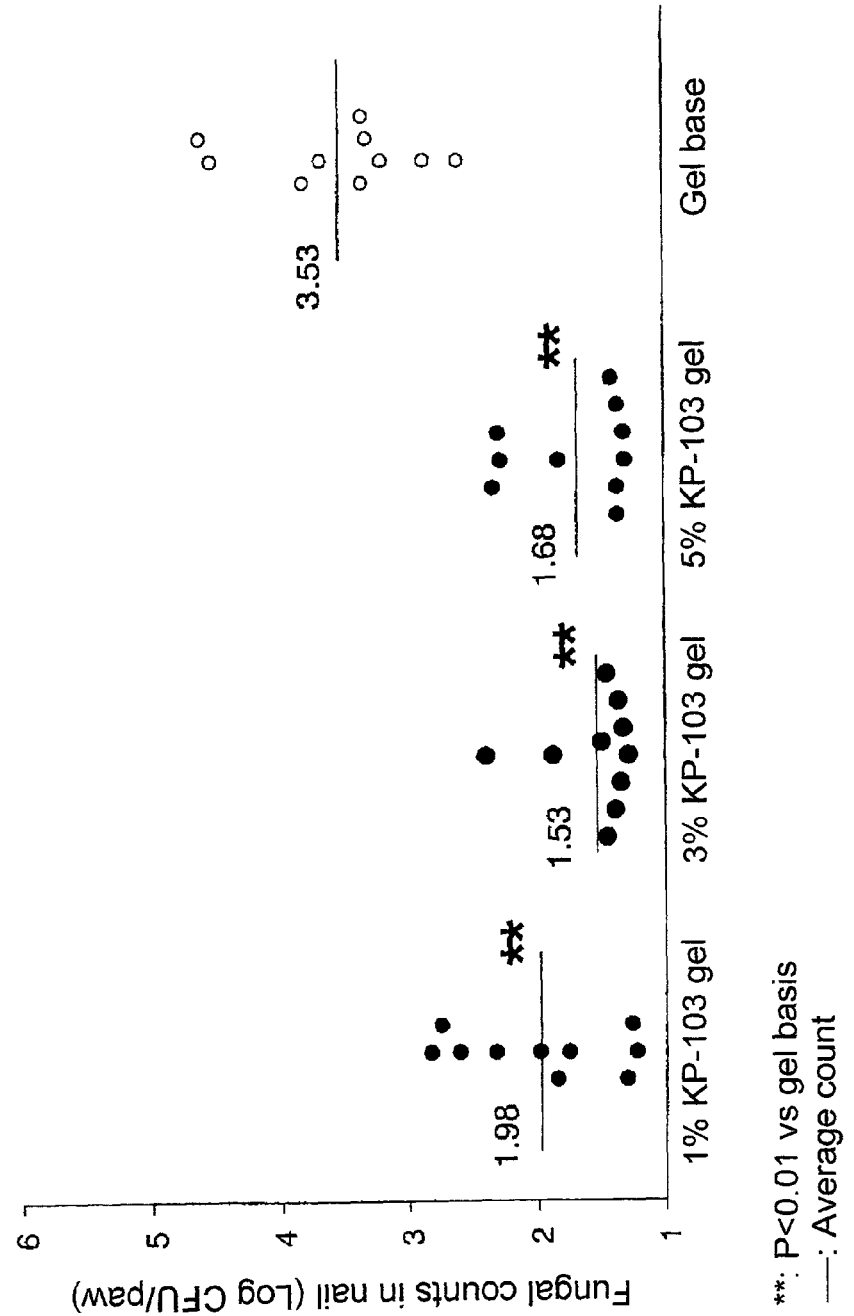
FIG. 4 shows the results of fungal count reduction in dermatophyte-infected guinea pig nail.

The fungal counts in the nail were analyzed for statistical significance between groups by one-way ANOVA, followed by Tukey's multiple comparison test. Likewise, the negative conversion rate of fungi in the nail was analyzed for statistical significance between groups by Fisher's direct probability test. A significance level of less than 5% (p<0.05) was considered as statistically significant. The results obtained are shown in Table 13 and FIG. 4.

TABLE 13

Therapeutic effect (dose dependence) in guinea pig tinea unguium model

| Analyte | Fungus-negative nail/ all infected nails | Average count in the nail (LogCFU ± SD) |
|---|---|---|
| Gel base | 0/10 | 3.53 ± 0.66 |
| 1% KP-103 gel preparation | 3/10 | 1.98 + 0.61** |
| 3% KP-103 gel preparation | 8/10** | 1.53 ± 0.34** |
| 5% KP-103 gel preparation | 6/10** | 1.68 ± 0.45** |

**p < 0.01 vs gel base

As shown in Table 13, all the three doses of KP-103 showed a higher reducing effect on fungal counts in the nail than in the gel base. There was no significant difference in this effect among the three doses. Moreover, in the treated groups receiving the 1%, 3% and 5% KP-103 gel preparations, their nails in 3, 8 and 6 paws out of 10 were found to be fungus-negative, respectively. The effects obtained at doses of 3% and 5% were each significantly higher than that of the gel base.

EXPERIMENTAL EXAMPLE 8

Stability Test 1

Figure 5:
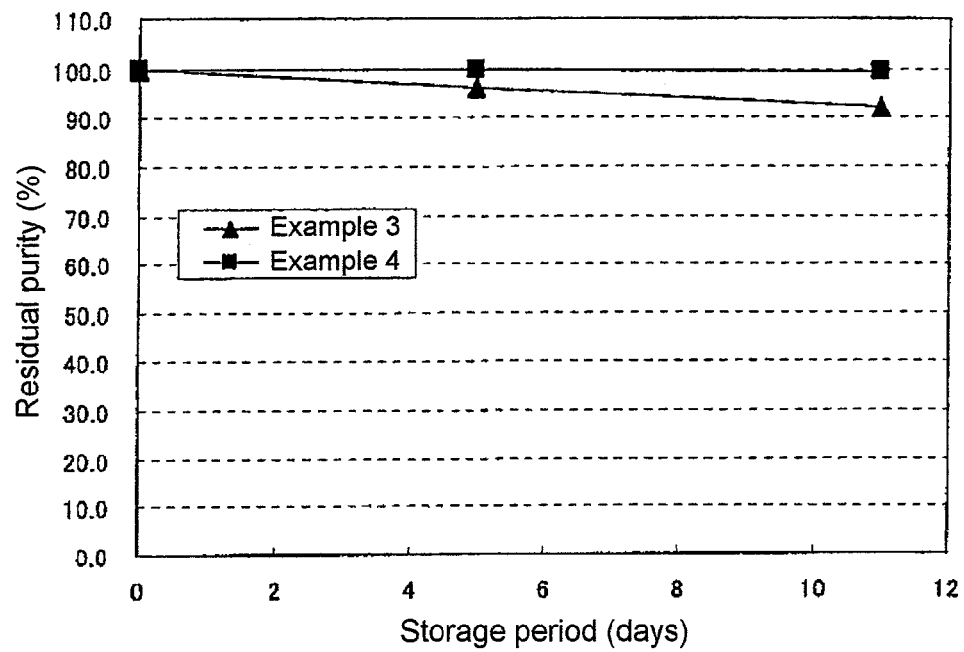
FIG. 5 shows the results of stability test.

The gel compositions of the present invention from Examples 3 and 4 were used and tested for their stability. The gel compositions were each filled into a glass ampule and subjected to stress testing at 70° C. under light-shielded conditions for 11 days. The results obtained are shown in FIG. 5.

The gel compositions of the present invention from Examples 5 and 12-15 were also subjected to the same stress testing as shown above.

As a result, the gel compositions from Examples 5 and 12-15 were found to have a residual purity of 92%, 93%, 92%, 94% and 92%, respectively.

These results indicated that the composition (gel preparation) of the present invention from each example had a residual purity of 90% or more even after storage at 70° C. for 11 days, thus ensuring sufficient stability.

EXPERIMENTAL EXAMPLE 9

Stability Test 2

The gel compositions of the present invention were each filled into a glass ampule and subjected to stress testing at 60° C. under light-shielded conditions for 1 month.

As a result, the gel compositions from Examples 4 and 7-11 were found to have a residual purity of 99%, 99%, 99%, 98%, 99% and 99%, respectively.

EXPERIMENTAL EXAMPLE 10

Stability Test 3

The gel compositions of the present invention were each filled into a glass ampule and subjected to stress testing at 40° C. under light-shielded conditions for 6 months.

As a result, all the gel compositions from Examples 4 and 8-10 were found to have a residual purity of 100%.

Industrial Applicability

As described above, the gel compositions of the present invention showed excellent permeation into the skin and nail and also showed a significantly higher effect on both reduction of fungal counts and negative conversion of fungi, when compared to KP-103 solutions. Namely, the present invention enables the development of a preparation by which KP-103 having an excellent bactericidal effect against fungi can be directly and rapidly absorbed and permeated into the nail.

In particular, there is no external preparation on the market, which serves as a potent therapeutic preparation for onychomycosis and produces a negative conversion effect on fungi in the nail. Thus, the present invention is a breakthrough that compensates the drawbacks of current therapy for onychomycosis treatment.

The invention claimed is:

1. A gel composition which comprises 0.01% to 10.0% by mass of (2R,3R)-2-(2,4-difluorophenyl)-3-(4-methylenepiperidin-1-yl)-1-(1H-1,2,4-triazol-1-yl)-butan-2-ol or an acid addition salt thereof, 0.01% to 10% by mass of a gel-forming polymer, 10.0% to 30.0% by mass of a permeation enhancer, 15.0% to 50.0% by mass of a $C_1$-$C_4$ alcohol and 30.0% to 70.0% by mass of a polyhydric alcohol, in which the ingredients are given in % by mass of the composition, and wherein the gel composition has a pH of about 6 to about 8, and is either aqueous or non-aqueous, provided that, if aqueous, the content of water is no more than 5% by mass of the composition.

2. A method of treating mycosis comprising administering to a patient in need thereof, a therapeutically effective amount of a composition comprising 0.01% to 10.0% by mass of (2R,3R)-2-(2,4-difluorophenyl)-3-(4-methylenepiperidin-1-yl)-1-(1H-1,2,4-triazol-1-yl)-butan-2-ol or an acid addition salt thereof, 0.01% to 10.0% by mass of a gel-forming polymer, 10.0% to 30.0% by mass of a permeation enhancer, 15.0% to 50.0% by mass of a $C_1$-$C_4$ alcohol and 30.0 to 70.0% by mass of a polyhydric alcohol, in which the ingredients are given in % by mass of the composition, and wherein the composition has a pH of about 6 to about 8, and is either aqueous or non-aqueous, provided that, if aqueous, the content of water is no more than 5% by mass of the composition.

3. The method of claim 2, wherein the mycosis is onchomycosis.

4. The gel composition according to claim 1, wherein the $C_1$-$C_4$ alcohol is one or more members selected from ethanol, isopropanol and butanol.

5. The gel composition according to claim 1, wherein the polyhydric alcohol is one or more members selected from glycerine, 1,3-butylene glycol, propylene glycol, dipropylene glycol and triethylene glycol.

6. The gel composition according to claim 1, wherein the permeation enhancer is one or more members selected from triacetin, sorbitan monooleate and polyoxyethylene sorbitan monooleate.

7. The gel composition according to claim 1, wherein the gel-forming polymer is a member of carboxyvinyl polymer.

8. The gel composition according to claim 1, wherein the gel-forming polymer is carboxyvinyl polymer.

9. The gel composition according to claim 1, wherein the content of the gel-forming polymer is 0.1% to 5.0% by mass of the composition.

10. The gel composition according to claim 1, which further comprises a neutralizing agent.

11. The method according to claim 2, wherein the $C_1$-$C_4$ alcohol is one or more members selected from ethanol, isopropanol and butanol.

12. The method according to claim 2, wherein the polyhydric alcohol is one or more members selected from glycerine, 1,3-butylene glycol, propylene glycol, dipropylene glycol and triethylene glycol.

13. The method according to claim 2, wherein the permeation enhancer is one or more members selected from triacetin, sorbitan monooleate and polyoxyethylene sorbitan monooleate.

14. The method according to claim 2, wherein the gel-forming polymer is a member of carboxyvinyl polymer.

15. The method according to claim 2, wherein the gel-forming polymer is carboxyvinyl polymer.

16. The method according to claim 2, wherein the content of the gel-forming polymer is 0.1% to 5.0% by mass of the composition.

17. The method according to claim 2, which further comprises a neutralizing agent.

* * * * *